US00PP23624P2

(12) United States Plant Patent
Sakazaki

(10) Patent No.: US PP23,624 P2
(45) Date of Patent: May 21, 2013

(54) *CAMPANULA* PLANT NAMED 'USCAMP10'

(50) Latin Name: ***Campanula* hybrid**
Varietal Denomination: USCAMP10

(75) Inventor: Ushio Sakazaki, Hikone (JP)

(73) Assignee: Amerinova Properties LLC, Bonsall, CA (US)

( * ) Notice: Subject to any disclaimer, the term of this patent is extended or adjusted under 35 U.S.C. 154(b) by 5 days.

(21) Appl. No.: 13/317,208

(22) Filed: Oct. 12, 2011

(51) Int. Cl.
*A01H 5/00* (2006.01)

(52) U.S. Cl.
USPC ..... Plt./414

(58) Field of Classification Search ..... Plt./414
See application file for complete search history.

*Primary Examiner* — Susan McCormick Ewoldt
(74) *Attorney, Agent, or Firm* — Cassandra Bright

(57) ABSTRACT

A new and distinct *Campanula* cultivar named 'USCAMP10' is disclosed, characterized by vigorous plant growth, dark, violet-blue flowers and a long flowering period. The new variety is a *Campanula*, normally produced as an outdoor ornamental plant for containers or gardens.

1 Drawing Sheet

Latin name of the genus and species: *Campanula* hybrid.
Variety denomination: 'USCAMP10'.

BACKGROUND OF THE INVENTION

The new cultivar was discovered as a result of a planned breeding program directed by the inventor, Ushio Sakazaki, a citizen of Japan. The seed parent is the unpatented *Campanula* hybrid 'Kent Belle' and the pollen parent is the unpatented variety *Campanula punctata* 'Kurokawae'. The cross resulting in 'USCAMP10' was made Jun. 20, 2003. The new variety was discovered Sep. 20, 2004, by the inventor in a non-commercial nursery in Hikone, Japan.

Asexual reproduction of the new cultivar 'USCAMP10' by vegetative division was first performed Oct. 14, 2004 at a non-commercial nursery in Hikone, Japan. Multiple generations have since been produced and have shown that the unique features of this cultivar are stable and reproduced true to type in successive generations. The new cultivar was first sold and made available to the public in April 2011.

SUMMARY OF THE INVENTION

The cultivar 'USCAMP10' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'USCAMP10' These characteristics in combination distinguish 'USCAMP10' as a new and distinct *Campanula* cultivar:

1. Vigorous and compact growth habit.
2. Large flowers.
3. Dark Violet-blue flowers.
4. Longer flowering period.

PARENT COMPARISON

Plants of the new cultivar 'USCAMP10' are similar to plants of the seed parent, *Campanula* hybid 'Kent Belle', in most horticultural characteristics, however, plants of the new cultivar 'USCAMP10' produce more branches than the seed parent. Plants of 'USCAMP10' are overall shorter than the seed parent, and produce longer flowers.

Plants of the new cultivar 'USCAMP10' are similar to plants of the pollen parent *Campanula punctata* 'Kurokawae' in most horticultural characteristics, however, plants of the new cultivar 'USCAMP10' are overall taller than the pollen parent. Flower color of the new variety is dark blue, whereas the pollen parent has light pink flower. Additionally, the new variety has grows more vigorously than the pollen parent.

COMMERCIAL COMPARISON

'USCAMP10' can be compared to the commercial variety *Campanula* 'Get Mee'®, unpatented. The two varieties are similar in most horticultural characteristics, however, plants of 'USCAMP10' produce larger flowers, of a darker blue. Additionally, plants of the new variety produce a different shaped foliage than the comparator.

'USCAMP10' can be compared to the commercial variety *Campanula carpatica* 'Clips Blue'®, unpatented. The two varieties are similar in most horticultural characteristics, however, plants of 'USCAMP10' produce flowers that are both narrower and longer. Additionally the flower color of 'USCAMP10' is darker.

BRIEF DESCRIPTION OF THE PHOTOGRAPH

The accompanying photograph in FIG. 1 illustrates in full color a of typical plant of 'USCAMP10' grown in a poly house, in Bonsall, Calif., in a commercial 6 inch container. The photographs was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'USCAMP10' plants grown in a poly house, in Bonsall, Calif., in a commercial 6 inch container. The growing temperature ranged from 60° F. to 75° F. daytime and 50° F. to 60° F. at night. No chemical treatments were given. Measurements and numerical values represent averages of typical plant types.

Botanical classification: *Campanula* hybrid 'USCAMP10'.

PROPAGATION

Time to initiate roots during summer: Approximately 4 days at temperatures between 18° C. and 32° C.

Time to initiate roots during winter: Approximately 5 days at temperatures between 18° C. and 24° C.

Time to produce a rooted cutting: 34 to 37 days.

Root description: Fibrous, moderate to free branching, rhizomes present. Rhizomes approximately 0.4 cm thick, colored near Greyed-Orange 164D.

PLANT

Pot size of plant described: 6 inch pot.

Age of plant described: Approximately 10 Weeks.

Growth habit: Low mounding.

In a container or in the ground: 6 inch container.

Height: Approximately 16 cm.

Plant spread: Approximately 45 cm.

Stem characteristics:

*Length of stems*.—Approximately 24 cm.

*Diameter of stems*.—Approximately 0.3 cm.

*Quantity of stems per plant*.—More than 30 basally emerging stems, lateral branching rare.

*Texture of stems*.—Hispid, hairs minute, not dense.

*Color of stems*.—Near RHS Yellow-Green 146C.

FOLIAGE

Leaf:

*Arrangement*.—Alternate.

*Quantity*.—Approximately 12 per main branch.

*Average length*.—Approximately 5.5 cm.

*Average width*.—Approximately 2.0 cm.

*Shape of blade*.—Broad lanceolate.

*Apex*.—Acute.

*Base*.—Broad attenuate.

*Margin*.—Denticulate.

*Texture of top surface*.—Mainly glabrous, rarely hispid.

*Texture of bottom surface*.—Hispid along veins.

*Leaf internode length*.—Approximately 2 to 4 cm.

*Color*.—Young foliage upper side: Near RHS Green 143A. Young foliage under side: Near RHS Green 137C. Mature foliage upper side: Near RHS Green 137A. Mature foliage under side: Near RHS Green 137D.

*Venation*.—Type: Pinnate. Venation color upper side: Near Yellow-Green 145A. Venation color under side: Near Yellow-Green 145C.

*Petiole*.—Sessile

FLOWER

Natural flowering season: Spring and Summer.

Begins flowering after how many months/weeks:

Inflorescence type and habit: Campanulate flowers, occurring either singly from leaf axils, or occurring as a cyme composed of 3 to 4 flowers.

*Cyme*.—Width: Approximately 8.5 cm. Height: Approximately 8.5 cm.

Rate of flower opening: Approximately days from bud to fully opened flower.

Flower longevity on plant: Days, after fully opened.

Quantity of flowers: Approximately 30 open flowers per mature plant.

Flower size:

*Diameter*.—Approximately 3.5 cm.

*Length*.—Approximately 6.5 cm.

Peduncle:

*Length*.—Approximately 2.0 cm.

*Diameter*.—Approximately 0.1 cm.

*Color*.—Near RHS Yellow-Green 144B, flushed with Greyed-Purple 187A.

*Texture*.—Very slightly hirsute.

Pedicel:

*Length*.—Range from Approximately 0.7 cm. to 2.0 cm.

*Diameter*.—Approximately 0.1 cm.

*Color*.—Near RHS Green 143C.

*Texture*.—Softly pubescent.

Corolla:

*Petal arrangement*.—Fused corolla.

*Shape*.—Campanulate, lobes approximately 0.9 cm deep.

*Margin*.—Entire.

*Apex*.—Acute.

*Petal quantity*.—5.

*Texture*.—Exterior glabrous, interior pubescent.

Color:

*Petals*.—When opening: Inner surface: Near RHS Violet-Blue N89C. Outer surface: Near RHS Violet-Blue 93C, margins darker, near 93A. Fully opened: Inner surface: Near RHS Violet-Blue 90B, Outer surface: Near RHS Violet-Blue 93B, with veins Violet-Blue N89B. Color Changes when aging: Darkens to Violet-Blue N92C.

Bud:

*Shape*.—Puffy, elongated sphere.

*Length*.—Approximately 2.5 cm.

*Diameter*.—Approximately 1.5 cm.

*Color*.—Near RHS Violet-Blue 91A.

Sepals:

*Quantity*.—5.

*Length*.—Approximately 0.6 cm.

*Width*.—Approximately 0.4 cm.

*Shape*.—Deltoid.

*Color*.—Interior Surface: Near RHS Green 143C. Exterior Surface: Near RHS Yellow-Green 144A.

*Texture*.—Pubescent.

Fragrance: None.

Persistence: Flower persistent.

REPRODUCTIVE ORGANS

Stamens:

*Number.*—5.

*Filament length.*—Approximately 0.2 cm.

*Filament color.*—Near RHS White 155C.

Anthers:

*Length.*—0.6 cm.

*Shape.*—Linear.

*Color.*—Near RHS White N155C.

*Pollen.*—Not observed to produce pollen.

Pistil:

*Number.*—1.

*Length.*—Approximately 3.0 cm.

*Style.*—Length: Approximately 0.8 cm. Color: Near RHS White N155D.

*Stigma.*—Shape: Linear. Length: Approximately 1.5 cm. Color: Near RHS White N155D. Ovary Color: Near RHS White N155D.

OTHER CHARACTERISTICS

Seeds and fruits: Not observed to date.

Disease/pest resistance: Neither resistance nor susceptibility to normal pests and diseases of *Campanula* observed to date.

Drought tolerance and temperature tolerance: Hardy perennial to at least −10° C. Upper temperature tolerance to at least 40° C. No tolerance for drought.

What is claimed is:

1. A new and distinct cultivar of *Campanula* plant named 'USCAMP10' as herein illustrated and described.

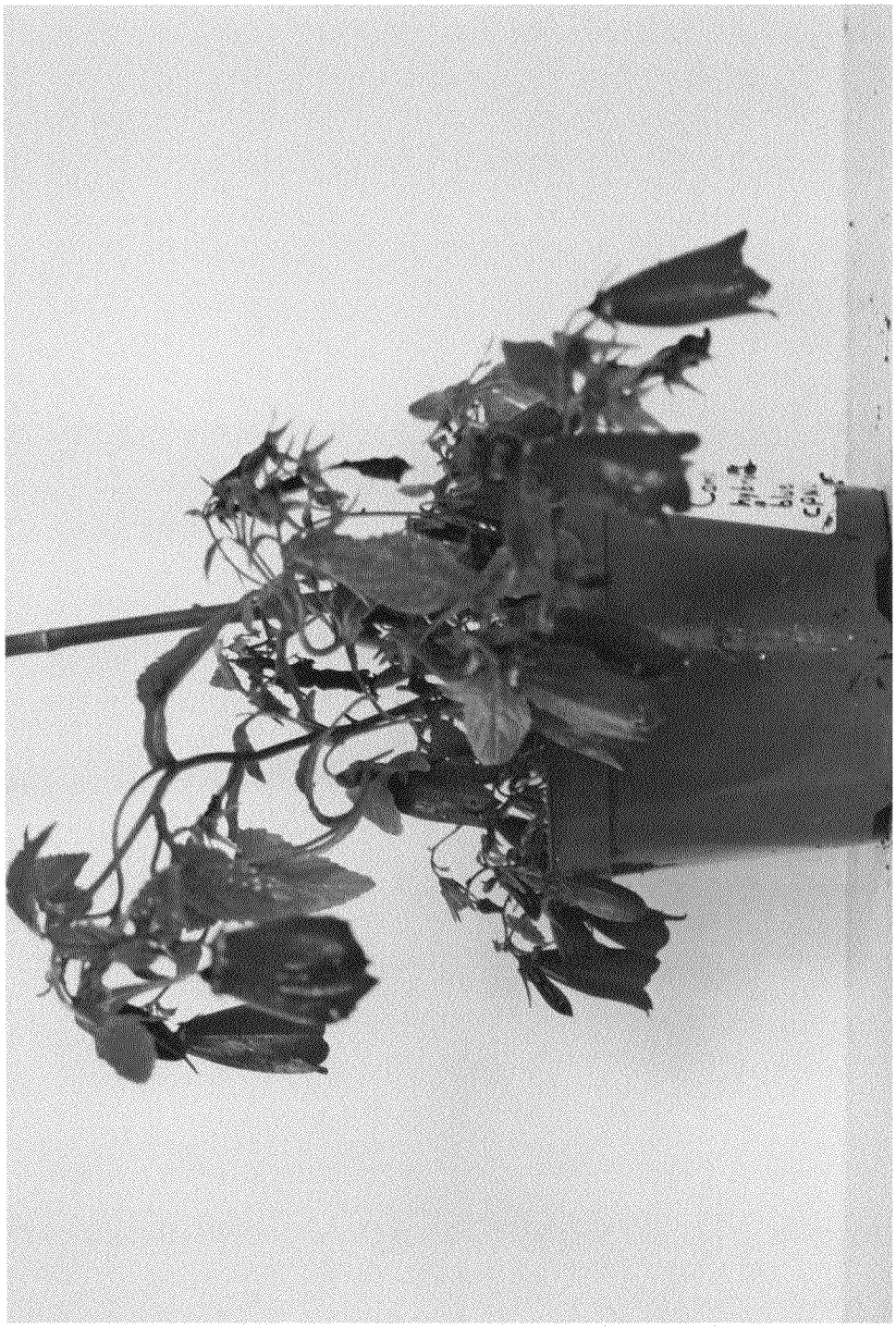

* * * * *